United States Patent [19]

Sudilovsky

[11] Patent Number: 4,912,096

[45] Date of Patent: Mar. 27, 1990

[54] METHOD FOR PREVENTING OR TREATING DEPRESSION EMPLOYING AN ACE INHIBITOR

[75] Inventor: Abraham Sudilovsky, Lawrenceville, N.J.

[73] Assignee: E. R. Squibb & Sons, Inc., Princeton, N.J.

[21] Appl. No.: 371,161

[22] Filed: Jun. 26, 1989

[51] Int. Cl.[4] .................... A61K 31/40; A61K 31/675
[52] U.S. Cl. ...................................... 514/91; 514/422; 514/423
[58] Field of Search ........................ 514/91, 422, 423

[56] References Cited

PUBLICATIONS

Deicken, R. F., "Captopril Treatment of Depression", Biol. Psychiatry, 1986; 21:1425-1428.

Zubenko, G. S., "Mood-Elevating Effect of Captopril in Depressed Patients", Am. J. Psychicatry 141: 110-11, 1984.

Germain, L. et al., "Treatment of Recurrent Unipolar Major Depression with Captopril", Biol. Psychiatry, 1988; 23:637-641.

Giàrdina, W. J. et al., "Positive Effects of Captopril in the Behavioral Despair Swim Test", Biol. Psychiatry 1989; 25:695-702.

Bosio, A. et al., "Antidepressant Activity of ACE-Inhibitors", TIPS, vol. 8, pp. 329-330, 1987 (Abstracts of 141st Annual Meeting of the American Psychiatric Assoc., Montreal, Canada, May 7-12, 1988).

Primary Examiner—Stanley J. Friedman
Attorney, Agent, or Firm—Burton Rodney

[57] ABSTRACT

A method is provided for inhibiting onset of or treating depression by administering an ACE inhibitor, which is (S)-1-[6-amino-2-[[hydroxy-(4-phenylbutyl)phosphenyl]oxy]-1-oxohexyl]-L-proline, fosinopril or zofenopril, alone or in combination with an antidepressant drug such as lithium, over a prolonged period of treatment.

8 Claims, No Drawings

METHOD FOR PREVENTING OR TREATING DEPRESSION EMPLOYING AN ACE INHIBITOR

FIELD OF THE INVENTION

The present invention relates to a method for preventing or treating depression by administering an ACE inhibitor, which is SQ 29,852, zofenopril, or fosinopril.

BACKGROUND OF THE INVENTION

The use of captopril, an angiotensin-converting enzyme inhibitor, for treating depression is disclosed in the following references:

Deicken, R. F., "Captopril Treatment of Depression," Biol Psychiatry, 1986; 21:1425-1428;

Zubenko, G. S., "Mood-Elevating Effect of Captopril in Depressed Patients," Am. J. Psychiatry 141:110-11, 1984;

Germain, L. et al, "Treatment of Recurrent Unipolar Major Depression with Captopril," Biol Psychiatry, 1988; 23:637-641;

Giardina, W. J. et al, "Positive Effects of Captopril in the Behavioral Despair Swim Test," Biol Psychiatry 1989; 25:695-702;

Bosio, A. et al, "Antidepressant Activity of ACE-Inhibitors," TIPS, Vol. 8, pp 329-330, 1987 (Abstracts of 141st Annual Meeting of the American Psychiatric Association, Montreal, Canada, May 7-12, 1988), discloses that captopril has antidepressant activity while enalapril does not. "These results indicate that ACE inhibitor activity is not related to psychotropic effect; . . ."

DESCRIPTION OF THE INVENTION

In accordance with the present invention, a method is provided for preventing or treating depression wherein an antidepressive effective amount of an angiotensin converting enzyme inhibitor which is SQ 29,852, zofenopril or fosinopril, alone or in combination with an antidepressant drug is systemically, such as orally or parenterally, administered.

Where a combination of ACE inhibitor and antidepressant drug is to be used, the ACE inhibitor will be employed in a weight ratio to the antidepressant drug of within the range of from about 0.1:1 to about 10:1 and preferably from about 0.4:1 to about 2.5:1.

The term "depression" as used herein is as defined in "A Quick Reference to Diagnostic Criteria from DSM-III-R, June, 1987," (American Psychiatric Association), and includes depressive disorders such as dysthymia (depressive neurosis), including primary and secondary types, major depression, and depressive disorder not otherwise specified, as well as bipolar disorders including bipolar disorder, mixed (manic and major depressive episodes), bipolar disorder, depressed, and bipolar disorder not otherwise specified.

The angiotensin converting enzyme inhibitor which may be employed herein includes substituted proline derivatives which include (S)-1-[6-amino -2-[[hydroxy-(4-phenylbutyl)phosphinyl]oxy]-1-oxohexyl]-L-proline (SQ 29,852), zofenopril add fosinopril.

(S)-1-[6-Amino-2-[[hydroxy(4-phenylbutyl)phosphinyl]oxy]-1-oxohexyl]-L-proline, and pharmaceutically acceptable salts thereof, its method of preparation, and its activity as an antihypertensive agent due to its angiotensin converting enzyme inhibition activity are described by Karanewsky et al in U.S. Pat. No. 4,745,196.

Zofenopril which chemically is named [1(R*),2α,4α]-1-[3-(benzoylthio)-2-methyl-1-oxopropyl]-4-(phenylthio)-L-proline has been reported as being an antihypertensive agent due to its angiotensin converting enzyme inhibition activity. Zofenopril, its pharmaceutically acceptable salts, and its method of preparation are described by Ondetti et al in U.S. Pat. No. 4 316,906.

Fosinopril which chemically is named (trans)-4-cyclohexyl-1-[[2-methyl-1-(1-oxopropoxy)propoxy]-(4-phenylbutyl)phosphinyl]acetyl]-L-proline has been reported as being an antihypertensive agent due to its angiotensin converting enzyme inhibition activity. Fosinopril, its pharmaceutically acceptable salts, and its method of preparation are described by Paetrillo in U.S. Pat. Nos. 4,337,201 and 4,384,123.

Examples of antidepressants suitable for use herein in conjunction with the ACE inhibitor in the treatment of manic-depression include lithium, doxepin HCl, amitriptyline HCl, amoxapine, trazodone HCl, perphenazine, chlordiazepoxide, isocarboxazid, maprotiline HCl, phenelzine sulfate, desipramine HCl, nortriptyline HCl, tranylcypromine sulfate, trimipramine maleate, imipramine HCl, protriptyline HCl, including mixtures thereof.

In carrying out the method of the present invention, the angiotensin converting enzyme inhibitor alone or in combination with the antidepressant drug may be administered to mammalian species, such as monkeys, dogs, cats, rats and humans, nd as such may be incorporated in a conventional systemic dosage form, such as a tablet, capsule, elixir or injectable. The above dosage forms will also include the necessary carrier material, excipient, lubricant, buffer, bulking agent (such as mannitol), anti-oxidants (ascorbic acid of sodium bisulfite) or the like. Oral dosage forms are preferred, although parenteral forms such as intramuscular, intraperitoneal, or intravenous are quite satisfactory as well.

The dose administered must be carefully adjusted according to age, weight and condition of the patient, as well as the route of administration, dosage form an regimen and the desired result.

Thus, for oral administration, a satisfactory result may be obtained employing the ACE inhibitor in an amount within the range of from about 0.005 mg/kg to about 100 mg/kg and preferably from about 0.01 mg/kg to about 25 mg/kg alone or in combination with the antidepressant drug in an amount within the range of from about 0.005 mg/kg to about 100 mg/kg and preferably from about 0.01 mg/kg to about 25 mg/kg with the ACE inhibitor and antidepressant drug being employed together in the same oral dosage form or in separate oral dosage forms taken at the same time.

A preferred oral dosage form , such as tablets or capsules, will contain the ACE inhibitor in an amount of from about 0.1 to about 500 mg, preferably from about 125 to about 200 mg, and more preferably from about 25 to about 150 mg, alone or with the antidepressant drug in a total amount of from about 1 to about 350 mg, preferably from about 2 to about 200 mg, and more preferably from about 30 to about 150 mg.

For parenteral administration, the ACE inhibitor will be employed in an amount within the range of from about 0.005 mg/kg to about 10 mg/kg and preferably from about 0.01 mg/kg to about 1 mg/kg, alone or with the antidepressant drug in a total amount within the range of from about 0.005 mg/kg to about 20 mg/kg and preferably from about 0.01 mg/kg to about 2 mg/kg.

The composition described above may be administered in the dosage forms as described above in single or divided doses of one to four times daily. It may be advisable to start a patient on a low dose combination and work up gradually to a high dose combination.

Tablets of various sizes can be prepared, e.g., of about 50 to 700 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of ACE inhibitor and antidepressant drug are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials maybe present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for onset of depression remains or the symptoms of depression continue. Sustained release forms of such formulations which may provide such amounts biweekly, weekly, monthly and the like may also be employed. A dosing period of at least one to two weeks are required o achieve minimal benefit.

The antidepressant activity of SQ 29,852, fosinopril and zofenopril may be seen from the Porsolt test as described by Giardina et al, supra, as well as in the tests described in the other references mentioned hereinbefore.

The following Examples represent preferred embodiments of the present invention.

EXAMPLE 1

An SQ 29,852 formulation suitable for oral administration in inhibiting onset of or treating depression is set out below.

1000 tablets each containing 100 mg of (S)-1-[6-amino-2-[[hydroxy(4-phenylbutyl)phosphinyl]oxy-1-oxohexyl]-L-proline were produced from the following ingredients.

| | |
|---|---|
| (S)-1-[6-Amino-2-[[hydroxy(4-phenyl-butyl)phosphinyl]oxy-1-oxohexyl]-L-proline (SQ 29,852) | 100 g |
| Corn starch | 50 g |
| Gelatin | 7.5 g |
| Avicel (microcrystalline cellulose) | 25 g |
| Magnesium stearate | 2.5 g |

The SQ 29,852 and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for inhibiting onset of or treating depression.

EXAMPLE 2

An injectable solution for use in inhibiting onset of or treating depression is produced as follows:

| | | |
|---|---|---|
| SQ 29,852 | 500 | mg |
| Methyl paraben | 5 | mg |
| Propyl paraben | 1 | mg |
| Sodium chloride | 25 | g |
| Water for injection qs. | 5 | l. |

The SQ 29,852, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 3

A zofenopril formulation suitable for oral administration in inhibiting onset of or treating depression is set out below.

1000 tablets each containing 100 mg of zofenopril are produced from the following ingredients.

| | |
|---|---|
| [1(S),4(S)]-1-[3-(benzoylthio)-2-methyl-1-oxopropyl-4-(phenylthio)-L-proline (zofenopril) | 100 g |
| Corn starch | 50 g |
| Gelatin | 7.5 g |
| Avicel (microcrystalline cellulose) | 25 g |
| Magnesium stearate | 2.5 g |

The zofenopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for inhibiting onset of or treating depression.

EXAMPLE 4

By substituting 100 g of fosinopril for the zofenopril in Example 3, 1000 tablets each containing 100 mg of the fosinopril are produced which is useful in inhibiting onset of or treating depression.

EXAMPLE 5

1000 tablets each containing 200 mg of fosinopril are produced from the following ingredients:

| | |
|---|---|
| Fosinopril | 200 g |
| Lactose | 100 g |
| Avicel | 150 g |
| Corn starch | 50 g |
| Magnesium stearate | 5 g |

The fosinopril, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in inhibiting onset of or treating depression.

EXAMPLE 6

An injectable solution for use in carrying out the method of this invention was prepared as follows:

| | |
|---|---|
| Zofenopril calcium | 500 mg |
| Methyl paraben | 5 mg |
| Propyl paraben | 1 mg |
| Sodium chloride | 25 g |
| Water for injection qs. | 5 l |

The zofenopril calcium, preservatives and sodium chloride are dissolved in 3 liters of water for injection add then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

Similar injectable solutions can be prepared by employing fosinopril sodium or (S)-1-[6-amino-2-[[hydroxy(4-phenylbutyl)phosphinyl]oxy]-1-oxohexyl]-L-proline, dilithium salt in place of the zofenopril calcium.

EXAMPLE 7

A SQ 29,852-lithium formulation suitable for oral administration in the treatment of depression is set out below.

1000 tablets each containing 100 mg of SQ 29,852 and 300 mg of lithium are produced from the following ingredients:

| | |
|---|---|
| SQ 29,852 | 100 g |
| Lithium carbonate | 300 g |
| Corn starch | 50 g |
| Gelatin | 7.5 g |
| Avicel (microcrystalline cellulose) | 25 g |
| Magnesium stearate | 2.5 g |

The SQ 29,852, lithium carbonate and corn starch are mixed with an aqueous solution of the gelatin. The mixture is dried and ground to a fine powder. The Avicel and then the magnesium stearate are admixed with the granulation. This is then compressed in a tablet to form 1000 tablets each containing 400 mg of active ingredients which is used for preventing or treating depression including biopolar disorders.

EXAMPLE 8

Tablets for use in treating or preventing bipolar disorders are prepared following the procedure of Example 7 except that zofenopril is employed in place of SQ 29,852.

EXAMPLE 9

Tablets for use in treating or preventing bipolar disorders are prepared following the procedure of Example 7 except that fosinopril is employed in place of SQ 29,852.

EXAMPLE 10

An injectable solution for use in treating or preventing bipolar disorders is produced as follows:

| | |
|---|---|
| SQ 29,852 | 500 mg |
| Lithium carbonate | 300 mg |
| Methyl paraben | 5 g |
| Propyl paraben | 1 g |
| Sodium chloride | 25 g |
| Water for injection qs. | 5 L. |

The SQ 29,852, lithium carbonate, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

What is claimed is:

1. A method for inhibiting onset of or treating depression in a mammalian specie, which comprises administering to a mammalian specie in need of such treatment an antidepressive effective amount of an angiotensin converting enzyme inhibitor which is (S)-1-[6-amino-2-[[hydroxy(4-phenylbutyl)phosphinyl]oxy]-1-oxohexyl]-L-proline, fosinopril or zofenopril or pharmaceutically acceptable salts thereof.

2. The method as defined in claim 1 wherein said angiotensin converting enzyme inhibitor is admixed with a pharmaceutically acceptable carrier therefor.

3. The method as defined in claim 1 wherein said angiotensin converting enzyme inhibitor is optionally administered with an antidepressant drug in single or separate dosage forms.

4. The method as defined in claim 1 wherein said angiotensin converting enzyme inhibitor is zofenopril.

5. The method as defined in claim 1 wherein said angiotensin converting enzyme inhibitor is fosinopril.

6. The method as defined in claim 1 wherein said angiotensin converting enzyme inhibitor is (S)-1-[6-amino-2-[[hydroxy(4-phenylbutyl)phosphinyl]oxy]-1-oxohexyl]-L-proline.

7. The method as defined in claim 1 wherein said angiotensin converting enzyme inhibitor is administered in single or divided doses of from about 0.1 to about 500 mg/one to four times daily and where present the antidepressant drug is administered in single or divided doses of from about 0.1 to about 300 mg/1 to 4 times daily.

8. The method as defined in claim 1 wherein said angiotensin converting enzyme inhibitor is (S)-1-[6-amino-2-[[hydroxy(4-phenylbutyl)phosphinyl]oxy]-1-oxohexyl]-L-proline and is administered systemically in an amount of from about 0.1 to about 500 mg/1 to 4 times a day.

* * * * *